(12) United States Patent
Asari et al.

(10) Patent No.: US 10,092,505 B2
(45) Date of Patent: Oct. 9, 2018

(54) ORAL FILM-FORM BASE AND PREPARATION

(71) Applicant: NITTO DENKO CORPORATION, Ibaraki-shi, Osaka (JP)

(72) Inventors: Daisuke Asari, Ibaraki (JP); Mitsuhiko Hori, Ibaraki (JP); Takuya Shishido, Ibaraki (JP)

(73) Assignee: NITTO DENKO CORPORATION, Ibaraki-shi, Osaka (JP)

( * ) Notice: Subject to any disclaimer, the term of this patent is extended or adjusted under 35 U.S.C. 154(b) by 0 days.

(21) Appl. No.: 13/737,255

(22) Filed: Jan. 9, 2013

(65) Prior Publication Data

US 2013/0177605 A1    Jul. 11, 2013

(30) Foreign Application Priority Data

Jan. 11, 2012    (JP) .................................. 2012-003625

(51) Int. Cl.
| | | |
|---|---|---|
| *A61K 9/46* | (2006.01) | |
| *A61K 9/00* | (2006.01) | |
| *A61K 47/02* | (2006.01) | |

(52) U.S. Cl.
CPC ............ *A61K 9/0007* (2013.01); *A61K 9/006* (2013.01); *A61K 47/02* (2013.01)

(58) Field of Classification Search
None
See application file for complete search history.

(56) References Cited

U.S. PATENT DOCUMENTS

| | | |
|---|---|---|
| 4,292,426 A | 9/1981 | Orii et al. |
| 4,639,368 A | 1/1987 | Niazi et al. |
| 4,687,660 A | 8/1987 | Baker et al. |
| 5,641,637 A | 6/1997 | Hudak et al. |
| 5,948,430 A | 9/1999 | Zerbe et al. |
| 6,156,343 A | 12/2000 | Morita et al. |
| 6,455,053 B1 | 9/2002 | Okada et al. |
| 6,531,151 B1 | 3/2003 | Besse |
| 6,649,186 B1 * | 11/2003 | Robinson ............. A61K 9/0007 424/466 |
| 2001/0006677 A1 * | 7/2001 | McGinity ............. A61K 9/0007 424/449 |
| 2003/0099690 A1 | 5/2003 | Awamura et al. |
| 2005/0008735 A1 | 1/2005 | Pearce |
| 2005/0079138 A1 | 4/2005 | Chickering et al. |
| 2005/0147653 A1 | 7/2005 | Yasuda et al. |
| 2005/0163830 A1 * | 7/2005 | Rademacher ........ A61K 9/0007 424/449 |
| 2005/0175675 A1 * | 8/2005 | Seibertz ........................ 424/443 |
| 2005/0186257 A1 | 8/2005 | Manegold et al. |
| 2005/0208110 A1 | 9/2005 | Singh et al. |
| 2006/0052340 A1 | 3/2006 | Tuzuki |
| 2006/0067207 A1 * | 3/2006 | Miyoshi ................ H04L 5/0021 370/210 |
| 2006/0078597 A1 * | 4/2006 | Jentzsch ................ C09K 15/34 424/442 |
| 2007/0098790 A1 | 5/2007 | Jiang |
| 2007/0122455 A1 | 5/2007 | Myer et al. |
| 2007/0178055 A1 | 8/2007 | Buch et al. |
| 2007/0237871 A1 | 10/2007 | Furusawa |
| 2007/0281003 A1 | 12/2007 | Fuisz et al. |
| 2007/0298105 A1 | 12/2007 | Hwang |
| 2008/0003267 A1 | 1/2008 | Spencer et al. |
| 2008/0200452 A1 | 8/2008 | Obermeier et al. |
| 2008/0268027 A1 | 10/2008 | Yang et al. |
| 2009/0155351 A1 | 6/2009 | Hejl et al. |
| 2009/0196908 A1 | 8/2009 | Lee et al. |
| 2009/0317531 A1 * | 12/2009 | Reh et al. ...................... 426/563 |
| 2010/0150986 A1 | 6/2010 | Nagaso et al. |
| 2011/0054043 A1 | 3/2011 | Funaki et al. |
| 2011/0111037 A1 | 5/2011 | Boit et al. |
| 2011/0182993 A1 | 7/2011 | Asari et al. |
| 2011/0293673 A1 * | 12/2011 | Asari ................... A61K 9/0056 424/400 |
| 2011/0293720 A1 | 12/2011 | General et al. |
| 2011/0300216 A1 * | 12/2011 | First ..................... A61K 9/0056 424/466 |
| 2011/0305768 A1 | 12/2011 | Mao et al. |

FOREIGN PATENT DOCUMENTS

| | | |
|---|---|---|
| CA | 1067407 A | 12/1979 |
| CA | 2339836 A1 | 3/2000 |
| CA | 2615533 A1 | 1/2007 |
| CN | 1652824 A | 8/2005 |
| CN | 101287445 A | 10/2008 |
| CN | 102300565 A | 12/2011 |

(Continued)

OTHER PUBLICATIONS

Sigma Aldrich L-ascorbic acid.*
European Search Report issued in counterpart EP Application No. 13000089.6, dated Jul. 12, 2013.
Office Action dated Apr. 21, 2015 from the Japanese Patent Office in counterpart application No. 2012-003625.
Office Action dated Mar. 10, 2015, issued by the Canadian Intellectual Property Office in Canadian application No. 2,750,617, which corresponds to U.S. Appl. No. 13/146,829.
Third Party Observation issued in JP Application No. 2010-548356, notified on Dec. 24, 2013, which corresponds to U.S. Appl. No. 13/146,829.
Third Notification of Office Action issued by the State Intellectual Property Office of China in CN Application No. 200980155744.8 dated Apr. 1, 2013, which corresponds to U.S. Appl. No. 13/146,829.

(Continued)

*Primary Examiner* — Robert A Wax
*Assistant Examiner* — Danah Al-Awadi
(74) *Attorney, Agent, or Firm* — Sughrue Mion, PLLC

(57) ABSTRACT

The present invention provides an oral film-form base which has a rapid dissolution profile in the mouth and sufficient film strength, and gives an improved taking property by foaming in the mouth. The oral film-form base includes an edible polymer soluble both in water and in an organic solvent having a solubility parameter of 9.7 or higher, a foaming agent, and an auxiliary foaming agent, wherein the foaming agent is foamable in the presence of water, and the foaming agent and the auxiliary foaming agent each are insoluble in the organic solvent, have an average particle size of 0.1 to 60 μm, and are included in particle states.

7 Claims, 1 Drawing Sheet

(56) References Cited

FOREIGN PATENT DOCUMENTS

| | | |
|---|---|---|
| EP | 1 522 225 A1 | 4/2005 |
| EP | 1 752 127 A1 | 2/2007 |
| FR | 2933299 A1 | 1/2010 |
| JP | 51-29218 | 3/1976 |
| JP | 07-187993 A | 7/1995 |
| JP | 10-179045 A | 7/1998 |
| JP | 11-116465 A | 4/1999 |
| JP | 11-116469 A | 4/1999 |
| JP | 2001-288074 A | 10/2001 |
| JP | 2002-523359 T | 7/2002 |
| JP | 2004-043450 A | 2/2004 |
| JP | 3496727 B2 | 2/2004 |
| JP | 2005-008568 A | 1/2005 |
| JP | 2005-021124 A | 1/2005 |
| JP | 2005-060244 A | 3/2005 |
| JP | 2005-511522 A | 4/2005 |
| JP | 2005-517722 A | 6/2005 |
| JP | 2005-342154 A | 12/2005 |
| JP | 2005-536443 A | 12/2005 |
| JP | 2005-537233 A | 12/2005 |
| JP | 2006-513269 A | 4/2006 |
| JP | 2007-500252 A | 1/2007 |
| JP | 2007-509172 A | 4/2007 |
| JP | 2007-528876 A | 10/2007 |
| JP | 2008-517935 A | 5/2008 |
| JP | 2008-169138 A | 7/2008 |
| JP | 2009-507854 A | 2/2009 |
| JP | 2009-510136 A | 3/2009 |
| JP | 2010-158173 A | 7/2010 |
| JP | 2010-172256 A | 8/2010 |
| JP | WO 2010/086989 * 8/2010 ............. A61K 47/32 |
| JP | 2010-209104 A | 9/2010 |
| JP | 4597662 B2 | 12/2010 |
| JP | 2001-504106 A | 3/2011 |
| JP | 2011-153113 A | 8/2011 |
| JP | 2001-318348 A | 11/2011 |
| KR | 10-2005-0000424 A | 1/2005 |
| KR | 10-2005-0088161 A | 9/2005 |
| KR | 10-2009-0128402 A | 12/2009 |
| RU | 2 316 316 C2 | 6/2005 |
| RU | 2256442 C2 | 7/2005 |
| WO | 98/20862 A1 | 5/1998 |
| WO | 01/70194 A1 | 9/2001 |
| WO | 03/030882 A1 | 4/2003 |
| WO | 03/030883 A1 | 4/2003 |
| WO | 03/070227 A1 | 8/2003 |
| WO | 03/101420 A1 | 12/2003 |
| WO | 2004/047794 A2 | 6/2004 |
| WO | 2004/066986 A1 | 8/2004 |
| WO | 2004/080499 A1 | 9/2004 |
| WO | 2005/039499 A2 | 5/2005 |
| WO | 2005/082048 A2 | 9/2005 |
| WO | 2006/031209 A1 | 3/2006 |
| WO | 2006/047365 A1 | 5/2006 |
| WO | 2006/114604 A2 | 11/2006 |
| WO | 2007/009801 A2 | 1/2007 |
| WO | 2007/030754 A2 | 3/2007 |
| WO | 2007/038926 A1 | 4/2007 |
| WO | 2008/089151 A2 | 7/2008 |
| WO | 2008/108940 A1 | 9/2008 |
| WO | 2008/149440 A1 | 12/2008 |
| WO | 2009/099830 A2 | 8/2009 |
| WO | 2009128433 A1 | 10/2009 |
| WO | 2010/015713 A1 | 2/2010 |
| WO | 2010/086989 A1 | 8/2010 |
| WO | 2010/144817 A1 | 12/2010 |
| WO | 2011/152875 A1 | 12/2011 |

OTHER PUBLICATIONS

Supplementary European Search Report issued in EP Application No. 09839222.8, dated Jul. 26, 2013, which corresponds to U.S. Appl. No. 13/146,829.

Fourth Notification of Office Action issued by the State Intellectual Property Office of China in CN Application No. 200980155744.8, dated Oct. 11, 2013, which corresponds to U.S. Appl. No. 13/146,829.
Office Action, dated Aug. 27, 2013, issued by the Japanese Patent Office, in Application No. 2010-548356, which corresponds to U.S. Appl. No. 13/146,829.
Office Action, dated Feb. 12, 2014, issued by the Japanese Patent Office, in Application No. 2010-548356, which corresponds to U.S. Appl. No. 13/146,829.
International Search Report for PCT/JP2009/054335 dated Mar. 31, 2009, which corresponds to U.S. Appl. No. 13/146,829.
Chinese Office Action issued in Application No. 200980155744.8 dated Mar. 22, 2012, which corresponds to U.S. Appl. No. 13/146,829.
Russian Office Action issued in Application No. 2011135837 dated Sep. 19, 2012, which corresponds to U.S. Appl. No. 13/146,829.
Office Action issued by State Intellectual Property Office of China in CN application 200980155744.8 dated Dec. 12, 2012, which corresponds to U.S. Appl. No. 13/146,829.
Russian Office Action dated Oct. 19, 2011, issued in Application No. 2011135837, which corresponds to U.S. Appl. No. 13/146,829.
Office Action dated Mar. 19, 2015, issued by the Russian Patent Office in Application No. 2011111666/15, which corresponds to U.S. Appl. No. 13/073,022.
Decision of Refusal dated Jan. 13, 2015, issued by the Japanese Patent Office in Japanese Application No. 2011049504, which corresponds to U.S. Appl. No. 13/073,022.
Decision of Refusal issued by the State Intellectual Property Office of the People's Republic of China in CN Application No. 201110078800.1. dated Nov. 3, 2014, which corresponds to U.S. Appl. No. 13/073,022.
Office Action dated May 22, 2014, issued by the State Intellectual Property Office of China in Chinese Application No. 201110078800.1, which corresponds to U.S. Appl. No. 13/073,022.
Second Notification of Office Action issued by the State Intellectual Property Office of China in CN Application No. 201110078800.1 dated Nov. 13, 2013, which corresponds to U.S. Appl. No. 13/073,022.
First Notification of Office Action issued by the State Intellectual Property Office of China in CN Application No. 201110078800.1 dated Apr. 1, 2013, which corresponds to U.S. Appl. No. 13/073,022.
Journal of Nanjing College of Traditional Chinese Medicine 1984, No. 4, pp. 53-55.
European Office Action dated May 10, 2012 issued in European Patent Application No. 11002555.8, which corresponds to U.S. Appl. No. 13/073,022.
The United States Pharmacopeia USP 24. The National Formulary NF 19, Jan. 1, 1999, p. 10, XP55026035.
European Search Report dated Jun. 29, 2011, issued in Application No. 11002555.8. which corresponds to U.S. Appl. No. 13/073,022.
Office Action dated Aug. 26, 2014, issued by the Japanese Patent Office in Japanese Application No. 2011-049504, which corresponds to U.S. Appl. No. 13/073,022.
Nasirov et al., Anabasne hydrochloride—A New Antismoking agent, New Drugs, 1978, pp. 281-283.
Kollidon, BASF, 1998, pp. 35-36.
ToxNet (http://toxnet.nlm.nih.gov/cgi-bin/sis/search/a?dbs+hsdb:@term+@DOCNO+783, accessed Aug. 17, 2013).
Communication dated Jan. 23, 2014, issued by the State Intellectual Property Office of the People's Republic of China in Application No. 201110078784.6, which corresponds to U.S. Appl. No. 13/072,972.
Communication dated Aug. 11, 2014, issued by the State Intellectual Property Office of the People's Republic of China in Application No. 201110030217.3, which corresponds to U.S. Appl. No. 13/014,245.
Communication dated Jan. 17, 2014, issued by the State Intellectual Property Office of the People's Republic of China in Application No. 201110030217.3, which corresponds to U.S. Appl. No. 13/014,245.
Communication dated May 21, 2013, issued by the State Intellectual Property Office of the People's Republic of China in Application No. 201110030217.3, which corresponds to U.S. Appl. No. 13/014,245.
Extended European Search Report for EP Application No. 11000618.6, dated Apr. 20, 2011, which corresponds to U.S. Appl. No. 13/014,245.

(56) References Cited

OTHER PUBLICATIONS

EP Office Action issued in Application No. 11000618.6 dated Nov. 2, 2012, which corresponds to U.S. Appl. No. 13/014,245.
Japanese Office Action issued in JP Application No. 2010-079429 dispatched on Dec. 17, 2013, which corresponds to U.S. Appl. No. 13/072,972.
First Notification of Office Action issued by the State Intellectual Property Office of China in CN Application No. 201110078784.6, dated May 23, 2013, which corresponds to U.S. Appl. No. 13/072,972.
Russian Office Action issued in Application No. 2011111665 dated Mar. 28, 2011, which corresponds to U.S. Appl. No. 13/072,972.
Stankovic, Ivan, Pullulan Chemical and Technical Assessment, Clinical and Technical Assessment 65$^{th}$ JECFA, 2002, pp. 1-8.
Perfetti et al., Influence of Polymer Coating on Strength of Particles: Polymer and Environmental Parameters, BioPowders Mini-Conference-Budapest, 2007, pp. 76-87.
Lliana et al., Diclofenac Solubility: Independent Determination of the Intrinsic Solubility of Three Crystal Forms, J. Med. Chem., 2007, 50, pp. 979-983.
Extended European Search Report dated Jul. 4, 2011, issued in EP Application No. 11002556.6, which corresponds to U.S. Appl. No. 13/072,972.
Developing Solid Oral Dosage Forms: Pharmaceutical Theory & Practice (edited by Qiu et al, Elvisar, 2009).
Yakuzaigaku, Pharmaceutics, ISBN 7-117-00026-0, Apr. 1996, pp. 236-238, 4 pages total.

Notification of Reexamination dated Mar. 31, 2016 from the State Intellectual Property Office of the P.R.C. issued in corresponding Application No. 201110078800.1.
First Notification of Office Action dated Mar. 24, 2016, from the State Intellectual Property Office of People's Republic of China in counterpart Application No. 201310007094.0.
Second Notification of Office Action dated Oct. 19, 2016, from the State Intellectual Property Office of People's Republic of China in counterpart Application No. 201310007094.0.
Reexamination Decision dated Sep. 18, 2016 from the State Intellectual Property Office of the P.R.C. in Application No. 201110078800.1, which corresponds to U.S. Appl. No. 13/073,022.
Communication dated Feb. 20, 2017, issued by the Canadian Patent Office in Canadian Application No. 2,735,592.
Final Office Action dated Jan. 10, 2017, from the USPTO in U.S. Appl. No. 13/073,022.
Non-Final Office Action dated Sep. 8, 2016, from the United States Patent and Trademark Office in U.S. Appl. No. 13/073,022.
Office Action dated Aug. 23, 2017 from the Russian Patent and Trademark Office in counterpart application No. 2013100165/15.
Office Action dated May 2, 2017, issued by the Russian Patent Office in counterpart Application No. 2013100165.
Notice of Submission of Opinion dated Jan. 4, 2018 from Korean Intellectual Property Office in counterpart application No. 10-2011-0027684.
First Examination Report dated May 24, 2018, from the Intellectual Property Office of India in counterpart application No. 6472/DELNP/2011.

\* cited by examiner

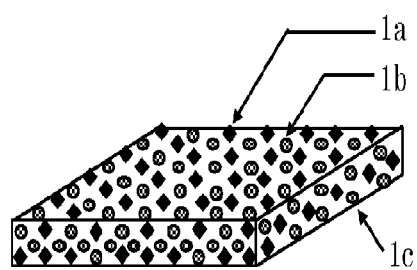

ORAL FILM-FORM BASE AND PREPARATION

CROSS REFERENCE TO RELATED APPLICATIONS

This application claims priority based on Japanese Patent Application No. 2012-003625 filed Jan. 11, 2012, the contents of which are incorporated herein by reference in their entirety.

TECHNICAL FIELD

The present invention relates to an oral film-form base that readily dissolves in the mouth; and a preparation including the oral film-form base and a drug contained in the base. More specifically, the present invention relates to an oral film-form base and preparation which contain fine particles of foaming ingredients which are foamable in the presence of water, and fine particles of mono- to hexasaccharide sugars and sugar alcohols thereof, which are dispersed in the oral film-form base. The oral film-form base and the oral film-form preparation rapidly dissolve or foam in the mouth such that the drug is well-absorbed via gastrointestinal tracts or oral mucosa.

BACKGROUND ART

At present, orally administered drugs are available in the market as solid preparations such as uncoated tablets, coated tablets, capsules, powders, and granules; liquid preparations such as liquids and emulsions; and the like. Moreover, orally disintegrating tablets and rapidly dissolving oral film-form preparations are already on the market as preparations that disintegrate in the mouth and are absorbed by the gastrointestinal tracts.

Orally administered film-, tape-, or sheet-form preparations that are to be disintegrated or dissolved by saliva without being chewed are already available as ethical pharmaceuticals or over-the-counter drugs (OTC drugs) overseas and in Japan.

For example, the following technologies relating to such film-form preparations are disclosed. Abase for a preparation which is obtained by dissolving, in a solvent, hydroxypropyl cellulose or a mixture of hydroxypropyl cellulose with polyvinylpyrrolidone, and a tannin substance, and then removing the solvent (see, Patent literature 1). A film-form troche which is obtained by laminating a coating layer (a) containing a water-soluble, non-hygroscopic polysaccharide and a softener, a drug layer (b) containing a drug and an edible water-soluble polymer, and a drug layer (c) containing a drug, an edible water-soluble polymer, and a tannin substance in the order of (a), (b), (c), (b), and (a) (see, Patent Literature 2). A rapidly dissolving film-form preparation which contains a drug and an edible polymer substance, has a film breaking strength of 200 to 3000 g/φ 7 mm and a film tensile strength of 200 to 3000 g/15 mm, and melts within 60 seconds in the mouth (see, Patent Literature 3). An oral film preparation that contains one of a pregelatinized starch and pullulan; an enzyme-modified starch; and a plasticizer (see, Patent Literature 4). A soluble film-form preparation which contains an active ingredient having a water solubility of about less than 1 g/4 mL at room temperature, and has a moisture content of about less than 15 wt % (see, Patent Literature 5). A film-form preparation which contains a drug, an edible water-soluble film forming agent, and low-substituted hydroxypropyl cellulose with a molar substitution degree of 0.05 to 1.0 (see, Patent Literature 6). A technology of preparing a rapidly dissolving preparation, which rapidly disintegrate or dissolve in the mouth or the like, by dissolving or dispersing a drug, saccharides, and polyvinylpyrrolidone in an organic solvent, and then removing the organic solvent (see, Patent Literature 7).

However, the film-form bases and preparations having been disclosed up to now are produced by dispersing or dissolving a drug in a water-soluble polymer. For example, Patent Literatures 3 and 4 teach addition of sugars or sugar alcohols in the bases and preparations. The sugars or sugar alcohols to be used are preliminary dissolved in a solvent or recrystallized. For this reason, those conventional oral film-form bases or preparations give a sticky sensation attributed to the water-soluble polymer when applied in the mouth and also when handled with fingers.

In order to solve the above problems, Patent Literatures 8 and 9 teach film-form preparations including fine particles of sugars and sugar alcohols supported in their original particle forms on a film. Moreover, Patent Literatures 10, 11, and the like, for example, teach other technologies to prepare rapidly dissolving preparations using foaming ingredients which foam upon contacting with water for achieving better taking property. However, the preparations have a two-layered structure (Patent Literature 10), or contain, as a foaming ingredient, a foaming agent that may foam in the presence of protonic solvents such as ethanol (Patent Literature 11), and thus have problems in terms of productivity and feasibility.

CITATION LIST

Patent Literature

Patent literature 1: JP 7-187993 A
Patent literature 2: JP 2001-288074 A
Patent literature 3: JP 2004-43450 A
Patent literature 4: JP 2005-21124 A
Patent literature 5: JP 2007-528876 T
Patent literature 6: JP 2008-169138 A
Patent literature 7: JP 11-116465 A
Patent literature 8: JP 2010-158173 A
Patent literature 9: PCT/JP2009/051511
Patent literature 10: JP 4597662 B
Patent literature 11: JP 2010-209104 A

SUMMARY OF INVENTION

Technical Problem

In consideration of the aforementioned current status, the present invention aims to provide oral film-form bases and oral film-form preparations, which have a rapid dissolution profile in the mouth and sufficient film strength, and provide better taking property by foaming in the mouth.

Solution to Problem

The present inventors have made intensive studies to solve the above problems, and have found that a preparation, if produced using the following film-form base, has a rapid dissolution profile in the mouth, better taking property achieved by foaming, and sufficient film strength, and provides an improved feel when applied in the mouth and an improved texture when handled with fingers. The film-form base is formed from a dispersion which is prepared by dispersing, in an organic solvent having a solubility parameter of 9.7 or higher, an edible polymer soluble both in water and in the organic solvent, and a foaming agent and an auxiliary foaming agent which are insoluble in the organic solvent and are foamable in the presence of water to provide the dispersion in which the foaming agent and the auxiliary foaming agent are dispersed in their original particle forms. Accordingly, the present inventors completed the present invention.

That is, the present invention relates to the following [1] to [18].

[1] An oral film-form base including an edible polymer soluble both in water and in an organic solvent having a solubility parameter of 9.7 or higher, a foaming agent, and an auxiliary foaming agent, wherein the foaming agent is foamable in the presence of water, and the foaming agent and the auxiliary foaming agent each are insoluble in the organic solvent, have an average particle size of 0.1 to 60 µm, and are included in particle states.

[2] The oral film-form base according to [1], wherein the foaming agent and the auxiliary foaming agent each have an average particle size of 0.1 µm to 30 µm.

[3] The oral film-form base according to [1] or [2], wherein the edible polymer is polyvinylpyrrolidone and/or hydroxypropyl cellulose.

[4] The oral film-form base according to [3], wherein the polyvinylpyrrolidone has a weight-average molecular weight of 2,500 to 3,000,000.

[5] The oral film-form base according to [3], wherein the hydroxypropyl cellulose has a weight-average molecular weight of 10,000 to 1,200,000.

[6] The oral film-form base according to [3] or [5], wherein the hydroxypropyl cellulose has a hydroxypropoxy substitution degree of 50 to 100%.

[7] The oral film-form base according to [1], [2], [3], [4], [5] or [6], wherein the foaming agent is at least one selected from the group consisting of sodium hydrogen carbonate, sodium carbonate, magnesium carbonate, ammonium hydrogen carbonate, ammonium carbonate, potassium carbonate, and calcium carbonate.

[8] The oral film-form base according to [1], [2], [3], [4], [5], [6] or [7], wherein the auxiliary foaming agent is at least one selected from the group consisting of L-ascorbic acid, potassium L-bitartrate, calcium dihydrogen pyrophosphate, disodium dihydrogen pyrophosphate, galacturonic acid, glucuronic acid, monosodium fumarate, potassium aluminum sulfate, sodium DL-malate, potassium dihydrogen phosphate, dipotassium hydrogen phosphate, sodium dihydrogen phosphate, and disodium hydrogen phosphate.

[9] The oral film-form base according to [1], [2], [3], [4], [5], [6], [7] or [8], further including particles of at least one selected from the group consisting of mono- to hexasaccharide sugars and sugar alcohols thereof each having an average particle size of 0.1 to 60

[10] An oral film-form preparation including the oral film-form base according to [1], [2], [3], [4], [5], [6], [7], [8] or [9], and a drug in the base.

[11] A method of producing an oral film-form base, including dissolving or dispersing, in an organic solvent having a solubility parameter of 9.7 or higher, an edible polymer soluble both in water and in the organic solvent, a foaming agent and an auxiliary foaming agent to prepare a dispersion, and forming a thin layer of the dispersion and then drying the thin layer, wherein the foaming agent is foamable in the presence of water, and the foaming agent and the auxiliary foaming agent each are insoluble in the organic solvent, and have an average particle size of 0.1 to 60 µm.

[12] A method of producing an oral film-form preparation, including dissolving or dispersing, in an organic solvent having a solubility parameter of 9.7 or higher, a drug, an edible polymer soluble both in water and in the organic solvent, a foaming agent, and an auxiliary foaming agent to prepare a dispersion, and forming a thin layer of the dispersion and then drying the thin layer, wherein the foaming agent is foamable in the presence of water, and the foaming agent and the auxiliary foaming agent each are insoluble in the organic solvent, and have an average particle size of 0.1 to 60 µm.

[13] A method of producing an oral film-form base, including dissolving, in a portion of an organic solvent having a solubility parameter of 9.7 or higher, an edible polymer soluble both in water and in the organic solvent to prepare a solution, mixing the solution with a mixture prepared by dispersing a foaming agent and an auxiliary foaming agent in the rest of the organic solvent to prepare a dispersion, and forming a thin layer of the dispersion and then drying the thin layer, wherein the foaming agent is foamable in the presence of water, and the foaming agent and the auxiliary foaming agent each are insoluble in the organic solvent, and have an average particle size of 0.1 to 60 µm.

[14] A method of producing an oral film-form preparation, including dissolving, in a portion of an organic solvent having a solubility parameter of 9.7 or higher, an edible polymer soluble both in water and in the organic solvent to prepare a solution, mixing the solution with a mixture prepared by dissolving or dispersing a drug, a foaming agent, and an auxiliary foaming agent in the rest of the organic solvent to prepare a dispersion, and forming a thin layer of the dispersion and then drying the thin layer, wherein the foaming agent is foamable in the presence of water, and the foaming agent and the auxiliary foaming agent each are insoluble in the organic solvent, and have an average particle size of 0.1 to 60 µm.

[15] The method of producing an oral film-form base according to [11] or [13], wherein the organic solvent having a solubility parameter of 9.7 or higher is an aprotic organic solvent.

[16] The method of producing an oral film-form base according to [11], [13] or [15], wherein the organic solvent having a solubility parameter of 9.7 or higher is acetone and/or ethanol.

[17] The method of producing an oral film-form preparation according to [12] or [14], wherein the organic solvent having a solubility parameter of 9.7 or higher is an aprotic organic solvent.

[18] The method of producing an oral film-form preparation according to [12], [14] or [17], wherein the organic solvent having a solubility parameter of 9.7 or higher is acetone and/or ethanol.

The oral film-form base of the present invention contains an edible polymer soluble both in water and in an organic solvent having a solubility parameter of 9.7 or higher, a foaming agent, and an auxiliary foaming agent.

Moreover, the oral film-form preparation of the present invention includes the oral film-form base of the present invention and a drug in the base.

Components commonly used in the oral film-form base and the oral film-form preparation of the present invention will be collectively described below.

FIG. 1 is a schematic view illustrating an embodiment of the oral film-form base of the present invention. As shown in FIG. 1, particles (1a) of a foaming agent and particles (1b) of an auxiliary foaming agent are considered to be dispersed uniformly in a film (1c) containing an edible polymer.

Moreover, in the case of the oral film-form preparation of the present invention, the particles (1a) of a foaming agent and the particles (1b) of an auxiliary foaming agent are considered to be dispersed uniformly in the film (1c) containing an edible polymer and a drug (not shown).

In the present invention, the edible polymer soluble both in water and in an organic solvent having a solubility parameter of 9.7 or higher is not particularly limited, and may be any edible polymer that is capable of forming a film, edible, not capable of dissolving the foaming agents and the auxiliary foaming agents described below, and soluble in the organic solvent. The term "edible" herein refers to a pharmaceutically acceptable state capable of being administered orally.

More specifically, preferable examples of the edible polymer include polyvinylpyrrolidone (hereinafter, PVP) and hydroxypropyl cellulose (hereinafter, HPC) because they exhibit sufficient solubility in water and in an organic solvent having a solubility parameter of 9.7 or higher, dissolve rapidly in the mouth, and enable use of the above organic solvent in production. HPC is more preferred because it has less hygroscopicity with regard to relative humidity than PVP, and is considered preferable from a practical standpoint.

Preferably, the weight-average molecular weight of the above PVP used as the edible polymer of the present invention is 2,500 to 3,000,000, and more preferably 2,500 to 1,200,000. If the weight-average molecular weight is less than 2,500, the stability and hygroscopicity of the oral film-form base and the oral film-form preparation to be obtained may be deteriorated. In contrast, if the molecular weight exceeds 3,000,000, the solubility in an organic solvent having a solubility parameter of 9.7 or higher may be poor.

Preferably, the weight-average molecular weight of the HPC used as the edible polymer of the present invention is 10,000 to 1,200,000, and more preferably 10,000 to 370,000. If the weight-average molecular weight is less than 10,000, the stability and hygroscopicity of the oral film-form base and the oral film-base preparation to be obtained may be deteriorated. In contrast, if the molecular weight exceeds 1,200,000, the solubility in an organic solvent having a solubility parameter of 9.7 or higher may be poor.

Meanwhile, the weight-average molecular weight of the PVP and HPC can be measured by gel permeation chromatography analysis.

Preferably, the hydroxypropoxy substitution degree in the HPC used as the edible polymer of the present invention is 50% to 100%. Here, the hydroxypropoxy substitution degree is a value determined in accordance with the quantitative method described in the section entitled "Hydroxypropyl cellulose" in the Official Monographs of the Fifteenth Edition of the Japanese Pharmacopoeia. More preferably, the hydroxypropoxy substitution degree in the HPC is at least 53.4%. If the hydroxypropoxy substitution degree is less than 53.4%, the solubility of the HPC in water and in an organic solvent having a solubility parameter of 9.7 or higher may be poor. The maximum hydroxypropoxy substitution degree in the HPC used in the present invention is preferably about 77.5% as defined in the Official Monographs of the Fifteenth Edition of the Japanese Pharmacopoeia.

Each of these edible polymers may be used alone, or two or more of the edible polymers may be used in combination. Commercially available edible polymers that are provided as pharmaceutical ones may be used as the edible polymer, for convenience. The proportion of the one or two or more edible polymers in the total amount of the oral film-form base or the oral film-form preparation according to the present invention is suitably 10 wt % to 80 wt %, and preferably 20 wt % to 70 wt %. If the proportion of the edible polymer is less than 10 wt %, the film may be fragile and show insufficient strength; in contrast, if the proportion exceeds 80 wt %, the polymer tends to cause a sticky sensation in the mouth.

The edible polymer soluble both in water and in an organic solvent having a solubility parameter of 9.7 or higher may be combined with an appropriate amount of an edible polymer soluble only in water or an edible polymer insoluble both in water and in an organic solvent. Examples of such edible polymers include polymers obtained from natural substances such as acacia gum, gum arabic, sodium alginate, casein, xanthan gum, guar gum, tamarind gum, tara gum, gellan gum, psyllium seed gum, dextran, dextrin, tragacanth gum, starch, pullulan, and pectin; semisynthetic polymers such as crystalline cellulose, methylcellulose, ethylcellulose, carboxymethylcellulose, carboxymethylcellulose sodium, carboxymethylcellulose calcium, sodium carboxymethyl starch, hydroxyethylcellulose, hydroxypropylmethylcellulose, and low-substituted hydroxypropyl cellulose; and synthetic polymers such as polyvinyl alcohol and a carboxyvinyl polymer. These polymers may be commercially available ones provided as pharmaceutical products.

In the present invention, a foaming agent is contained together with the edible polymer.

The foaming agent to be used is one which is insoluble in an organic solvent having a solubility parameter of 9.7 or higher, and is foamable in the presence of water. A foaming agent with the aforementioned property can be contained in particle states. The reason for this is described below.

The foaming agent is preferably one that generates carbon dioxide gas or ammonia gas in the presence of water, and examples thereof include sodium hydrogen carbonate, sodium carbonate, magnesium carbonate, ammonium hydrogen carbonate, ammonium carbonate, potassium hydrogen carbonate, potassium carbonate, calcium carbonate, and ammonium chloride. Any of these may be used alone, or two or more of these may be used in combination.

Since ammonium hydrogen carbonate and ammonium carbonate have slight ammonia odor, sodium hydrogen carbonate, sodium carbonate, magnesium carbonate, potassium carbonate, and calcium carbonate are preferred from a practical point of view.

Moreover, in the present invention, an auxiliary foaming agent is contained together with the foaming agent.

The auxiliary foaming agent is one that is insoluble in the organic solvent having a solubility parameter of 9.7 or higher, and allows the foaming agent to generate carbon dioxide gas or ammonia gas. The auxiliary foaming agent with the above property can be contained in particle states. The reason for this is described below.

Examples of the auxiliary foaming agent include L-ascorbic acid, L-aspartic acid, L-glutamic acid, potassium L-bitartrate, galacturonic acid, glucuronic acid, calcium dihydrogen pyrophosphate, monosodium fumarate, potassium aluminum sulfate, sodium DL-malate, potassium dihydrogen phosphate, dipotassium hydrogen phosphate, sodium dihydrogen phosphate, and disodium hydrogen phosphate. Any of these may be used alone, or two or more of these may be used in combination.

In consideration also of taste upon taking, the auxiliary foaming agent is most preferably L-aspartic acid, L-glutamic acid, potassium L-bitartrate, galacturonic acid, glucuronic acid, calcium dihydrogen pyrophosphate, monosodium fumarate, potassium aluminum sulfate, sodium dihydrogen phosphate, or disodium hydrogen phosphate.

Moreover, in the present invention, glucono-δ-lactone may be used as the auxiliary foaming agent because, although it is soluble in an organic solvent having a solubility parameter of 9.7 or higher, its auxiliary foaming function is secondary, and thus unexpected foaming of the foaming agent during preparation can be prevented. Glucono-δ-lactone is suitably used as an auxiliary foaming agent from a view point of taste upon taking.

In the present invention, the foaming agent and the auxiliary foaming agent are contained in particle states, and have an average particle size of 0.1 to 60 μm. If the foaming agent and the auxiliary foaming agent have an average particle size of less than 0.1 μm, the particles may aggregate, resulting in partial unevenness in the flexibility of the oral film-form base or oral film-form preparation. If the particles having an average particle size of more than 60 μm are contained in the film-form base or preparation of practical thickness, the flexibility of the base or the preparation may be different in some places, resulting in inferior film strength. Moreover, the foaming agent and the auxiliary foaming agent preferably have an average particle size of 0.1 to 30 μm.

In the present invention, particles of the following mono- to hexasaccharide sugars and sugar alcohols thereof which are insoluble in an organic solvent having a solubility parameter of 9.7 or higher may be contained as well as the edible polymer soluble both in water and in an organic solvent having a solubility parameter of 9.7 or higher and the foaming agent and the auxiliary foaming agent insoluble in an organic solvent having a solubility parameter of 9.7 or higher.

Examples of the monosaccharides include: aldotetroses such as erythrose and threose; aldopentoses such as ribose, lyxose, xylose, and arabinose; aldohexoses such as allose, talose, gulose, glucose, altrose, mannose, galactose, and idose; ketotetroses such as erythrulose; ketopentoses such as xylulose and ribulose; and ketohexoses such as psicose, fructose, sorbose, and tagatose. Examples of the disaccharides include: α-diglucosides such as trehalose, kojibiose, nigerose, maltose, and isomaltose; β-diglucosides such as isotrehalose, sophorose, laminaribiose, cellobiose, and gentiobiose; α,β-diglucocides such as neotrehalose; lactose; sucrose; and isomaltulose (palatinose). An example of the trisaccharides is raffinose. Examples of the tri- to hexasaccharide oligosaccharides include cyclic oligosaccharides such as fructooligosaccharides, galactooligosaccharides, xylooligosaccharides, isomaltooligosaccharides, chitin oligosaccharides, chitosan oligosaccharides, oligoglucosamine, and cyclodextrins.

Examples of the monosaccharide alcohols include: tetritols such as erythritol, D-threitol, and L-threitol; pentitols such as D-arabinitol and xylitol; hexitols such as D-iditol, galactitol (dulcitol), D-glucitol (sorbitol), and mannitol; and cyclitols such as inositol. Examples of the disaccharide alcohols include maltitol, lactitol, and reduced palatinose (isomalt). Examples of the oligosaccharide alcohols include pentaerythritol and reduced maltose syrup.

Mono- to trisaccharides and sugar alcohols thereof are preferably used from the standpoint of the ease of dissolution in the mouth of the oral film-form base and the oral film-form preparation according to the present invention. More specifically, lactose, erythritol, xylitol, mannitol, and reduced palatinose (isomalt) which have low hygroscopicity are more preferable. In the present invention, one or two or more compounds selected from the above mono- to hexasaccharide sugars and sugar alcohols thereof may be used.

In the present invention, the above mono- to hexasaccharide sugars and sugar alcohols thereof preferably have an average particle size of 0.1 to 60 μm. If the mono- to hexasaccharide sugars and sugar alcohols thereof have an average particle size of less than 0.1 μm, the particles may aggregate, resulting in partial unevenness in the flexibility of the oral film-form base or oral film-form preparation. If the particles having an average particle size exceeding 60 μm are contained in the oral film-form base or the oral film-form preparation of practical thickness, the flexibility of the base or the preparation may be different in some places. The mono- to hexasaccharide sugars and sugar alcohols thereof preferably have an average particle size of 0.1 to 30 μm.

The average particle sizes of the foaming agent, the auxiliary foaming agent, and the mono- to hexasaccharide sugars and sugar alcohols thereof herein refer to 50 vol % average particle sizes determined by a particle size analysis meter in a manner described below.

Namely, 20000 particles of each material are measured by a dry method with the particle size analysis meter (produced by Malvern Instruments Ltd.), and then the equivalent circle diameter is measured. Then, the 50 vol % average particle size is measured.

The foaming agent and the auxiliary foaming agent each preferably constitute 1 wt % to 40 wt %, and more preferably 2 wt % to 30 wt %, of the whole weight of the base or preparation.

If the amount of the foaming agent and the amount of the auxiliary foaming agent are each less than 1 wt % relative to the whole weight, sensation of foaming is almost unnoticeable in the mouth. Therefore, improvement of the taking property is not sufficiently achieved. If the amount exceeds 40 wt %, unless the average particle size of the foaming agent and the auxiliary foaming agent is considerably reduced, the shape retention properties and the like of the oral film-form base and the oral film-form preparation may be deteriorated. Moreover, since a smaller particle diameter increases the surface area, foaming due to humidity may occur during production.

The mono- to hexasaccharide sugars and sugar alcohols thereof preferably constitute 1 wt % to 80 wt %, more preferably 5 wt % to 60 wt %, of the whole weight of the base or preparation. In the oral film-form base or the oral film-form preparation of practical thickness, if the amount of the mono- to hexasaccharide sugars and sugar alcohols thereof is less than 1 wt %, sufficient improvement is not seen in the properties of dissolution profile in the mouth, film strength, a sticky sensation attributed to water-soluble polymers in the mouth, and a feel when handled with fingers. An amount exceeding 80 wt % may deteriorate the shape retention properties and the like of the oral film-form base or oral film-form preparation, unless the average particle size of the mono- to hexasaccharide sugars and sugar alcohols thereof is significantly reduced. As the foregoing foaming agent, auxiliary foaming agent, and mono- to hexasaccharide sugars and sugar alcohols thereof, commercially available products provided for pharmaceutical use are conveniently utilized, or those sized so that the average particle size lies within the above range may be used. Also, commercially available products can be used after sizing so that the average particle sizes lie within the above range. Meanwhile, adjustment of the average particle size may be carried out by methods such as pulverization, granulation through dry granulation, wet granulation or the like, and classification using a sieve, a mechanical classifier or the like.

The solubility of the edible polymer, the foaming agent, the auxiliary foaming agent, the mono- to hexasaccharide sugars and sugar alcohols thereof used in the present invention in water or in an organic solvent having a solubility parameter of 9.7 or higher is described by the following terms. That is, when an amount of 100 mL or more of the organic solvent or water is necessary to dissolve 1 g of a solute at 20° C., then the solute is "insoluble." In contrast, when an amount of less than 5 mL of the organic solvent or water is necessary to dissolve 1 g of a solute at 20° C., then the solute is "soluble." When an amount of less than 3 mL of water or the organic solvent is necessary, then the solute is "easily soluble." Meanwhile, the mono- to hexasaccharide sugars and sugar alcohols thereof used in the present invention are known to have low solubility in the organic solvent, and have lower solubility as the temperature of the organic solvent increases. Hence, by increasing the temperature of the organic solvent to lower the solubility, it is possible to stabilize the mono- to hexasaccharide sugars and sugar alcohols thereof in particle states.

In the present invention, the edible polymer is soluble in water and in an organic solvent having a solubility parameter of 9.7 or higher, while the foaming agent and the auxiliary foaming agent are insoluble in the organic solvent. As described later, the oral film-form base and the oral film-form preparation are produced using the aforementioned organic solvent. Thus, the edible polymer is dissolved while the foaming agent and the auxiliary foaming agent are not dissolved in the production process. Accordingly, the oral film-form base and the oral film-form preparation of the present invention have a rapid dissolution profile in the mouth and sufficient film strength.

Moreover, in the case of containing the aforementioned mono- to hexasaccharide sugars and sugar alcohols thereof, since the mono- to hexasaccharide sugars and sugar alcohols thereof are not dissolved in the production process, the oral film-form base and the oral film-form preparation of the present invention do not give a sticky sensation attributed to the water-soluble polymer when applied in the mouth or when handled with fingers, unlike conventional oral film-form base or the like.

The oral film-form base and the oral film-form preparation of the present invention may optionally contain a suitable amount of additive(s) such as a plasticizer (e.g., polyethylene glycol), a surfactant, a stabilizer, a preservative, an antioxidant, a fragrance, a flavor, a sweetener, and a colorant, as well as the edible polymer, the foaming agent, the auxiliary foaming agent, and the mono- to hexasaccharide sugars and sugar alcohols thereof.

The oral film-form preparation of the present invention contains a drug in addition to the oral film-form base of the present invention.

The drug to be contained in the oral film-form preparation of the present invention is not particularly limited as long as it can be orally administrated. Examples thereof include antineoplastics, antiinflammatory drugs, antiallergic drugs, antidiabetic drugs, antihyperlipidemic drugs, bone/calcium metabolic drugs, antihypertensive drugs, antianginal drugs, antiarrhythmic drugs, vasodilator drugs, diuretics, bronchodilators, antiasthmatic drugs, antitussives, expectorant drugs, digestants, gastrointestinal function regulators, antipeptic ulcer drugs, drugs for bowel disease, laxatives, antipsychotics, antidepressants, mood stabilizers, psychostimulants, hypnotics, antianxiety drugs, antiepileptics, drugs for migraine, antiemetics, antidinics, antiparkinson drugs, cerebral ameliorators, antidementia drugs, antibacterial drugs, antiviral drugs, antifungal drugs, drugs for frequent urination and voiding disorders, and drugs for urinary incontinence. The amount of the drug to be contained will differ depending on the kind and titer of the drug and the symptom of the patient to take the preparation, or the like. Still, in consideration of the required dosage, or the like, the amount is normally 0.1 wt % to 60 wt % of the whole amount of the oral film-form preparation.

Specific examples of the drug include zolmitriptan, diphenhydramine, tamuslosin, granisetron, tolterodine, scopolamine, famotidine, candesartan cilexetil, pioglitazone, amlodipine, donepezil, montelukast, pranlukast, and salts thereof.

The drug preferably does not taste bitter because the oral film-form preparation of the present invention is to be administrated orally, but drugs that taste bitter can also be suitably used by performing a bitterness masking technique, for example, microencapsulation, or by adding a bitterness blocking agent, sweetener, flavoring, or fragrance. Moreover, many of the auxiliary foaming agents usable in the present invention give sourness, and many of the mono- to hexasaccharide sugars and sugar alcohols thereof give sweetness, and can be expected to provide a bitterness masking effect on the drug.

The thickness of the oral film-form base and the oral film-form preparation is not particularly limited, but is preferably 30 μm to 300 μm. If the thickness is smaller than 30 μm, the film strength may decrease and thus the handling properties may deteriorate. If the thickness exceeds 300 μm, the preparation may require more time to dissolve in the mouth, thereby not dissolving easily.

The planar shape of the oral film-form base and the oral film-form preparation of the present invention may be a common shape such as a rectangle, a square, a circle, and an ellipse.

The oral film-form base according to the present invention can be produced by dissolving or dispersing, in an organic solvent having a solubility parameter of 9.7 or higher, an edible polymers soluble both in water and in the organic solvent, a foaming agent, and an auxiliary foaming agent to prepare a dispersion, and forming a thin layer of the dispersion and then drying the thin layer.

The aforementioned method of producing the oral film-form base of the present invention is one aspect of the present invention.

Moreover, the oral film-form preparation of the present invention can be produced by dispersing a drug together with the foaming agent and other components in the preparation of the dispersion.

The aforementioned method of producing the oral film-form preparation of the present invention is also one aspect of the present invention.

In order to control the dissolution time and taking property (sticky sensation) in the production method of the oral film-form base of the present invention and the oral film-form preparation of the present invention, mono- to hexasaccharide sugars and sugar alcohols thereof may further be added prior to addition of the foaming agent and the auxiliary foaming agent, and are then dissolved or dispersed in a manner similar to the above.

The oral film-form base of the present invention can also be produced by, for example, dissolving, in a portion of an organic solvent having a solubility parameter of 9.7 or higher, an edible polymer soluble both in water and in the organic solvent to prepare a solution, mixing the solution with a mixture prepared by dispersing a foaming agent and an auxiliary foaming agent in the rest of the organic solvent to prepare a dispersion, and forming a thin layer of the dispersion and then drying the thin layer.

The aforementioned method of producing the oral film-form base is another embodiment of the present invention.

Moreover, the oral film-form preparation can be produced by dispersing a drug together with the foaming agent and other components in the rest of the organic solvent in the preparation of the dispersion.

The aforementioned method of producing the oral film-form preparation of the present invention is also another embodiment of the present invention.

In the preparation of the dispersion in the method of producing the oral-film base according to the aforementioned another embodiment of the present invention and in the method of producing the oral film-form preparation according to the aforementioned another embodiment of the present invention, when the foaming agent and the auxiliary foaming agent are dispersed in the rest of the organic solvent, preferably the foaming agent and the auxiliary foaming agent are previously subjected to treatments such as pulverization, granulation, and classification to adjust the average particle sizes thereof so that they are dispersed evenly.

If necessary, in the aforementioned step, the mono- to hexasaccharide sugars and sugar alcohols thereof are preferably subjected to treatments such as pulverization, granulation, and classification to adjust the average particle sizes so that they are dispersed evenly in the rest of the organic solvent.

Moreover, the amount of the organic solvent used for dissolving the edible polymer is preferably from about 1 to 3 weight times of the edible polymer.

In forming a thin layer of the dispersion and drying the thin layer in the method of producing the oral film-form base of the present invention and the method of producing the oral film-form preparation of the present invention, and in the method of producing the oral film-form base and the method of producing the oral film-form preparation according to the other embodiments of the present invention, preferably an appropriate amount of the dispersion is spread onto a conventional release film made of polystyrene or polyethylene terephthalate.

Moreover, the optional components such as plasticizers maybe appropriately added in the preparation of the dispersion.

Conventional methods, though not limited thereto, may be exemplified for the method of forming a thin layer and the method of drying the thin layer in the method of producing the oral film-form base of the present invention and the method of producing the oral film-form preparation of the present invention, and in the method of producing the oral film-form base and the method of producing the oral film-form preparation according to the other embodiments of the present invention.

The dried thin layer is cut into a desired shape and size, and is vacuum sealed as needed so that the oral film-form film base or the oral film-form preparation can be produced.

In the present invention, the organic solvent having a solubility parameter of 9.7 or higher is not particularly limited as long as the foaming agent, the auxiliary foaming agent, and preferably sugars or sugar alcohols are insoluble but the edible polymer is soluble in the organic solvent. Examples of such an organic solvent include methanol, ethanol, isopropanol, propylene glycol, methylene chloride, and acetone. Any one selected from these may be used alone, or two or more of these may be used in combination. Furthermore, lower alcohols such as methanol, ethanol, and isopropanol, methylene chloride, and acetone are more preferably used.

Preferably, these organic solvents are used after undergoing dehydration treatment. Moreover, in the case where foam is generated in the dispersion during production of the oral film-form base or the oral film-form preparation, the dispersion is preferably deaerated by leaving it to stand overnight or by vacuum deaeration.

In the present invention, the term "solubility parameter" (SP value) refers to the square root of the heat of evaporation (cal/cm$^3$) required for one mole by volume of the liquid to evaporate. Table 1 shows the solubility parameter of water and organic solvents which can be used in the present invention.

The solubility parameter of the organic solvent which can be used in the present invention is preferably 9.7 to 20, and more preferably 9.7 to 15. An organic solvent having a solubility parameter exceeding 20 is not preferable for the purpose of the present invention because it may possibly dissolve foaming agents, auxiliary foaming agents, sugars or sugar alcohols.

TABLE 1

| Solvent | Solubility parameter (SP value) |
| --- | --- |
| Methanol | 14.5~14.8 |
| Ethanol | 12.7 |
| Isopropanol | 11.5 |
| Propylene glycol | 14.3 |
| Methylene chloride | 9.7 |
| Acetone | 10.0 |
| Water | 23.4 |

Advantageous Effects of Invention

The oral film-form base or the oral film-form preparation of the present invention contains a foaming agent and an auxiliary foaming agent each in a particle state, and have a rapid dissolution profile in the mouth and sufficient film strength. Moreover, as compared with conventional products, the base and preparation of the present invention have apparently improved properties such as a reduced sticky sensation attributed to the edible polymer when applied in the mouth, improved taking property due to foaming, and better feel when handled with fingers.

Namely, by evenly dispersing the foaming agent and the auxiliary foaming agent in particle states, it is possible to clearly improve only the properties that need to be improved relating to taking of the base and the preparation, such as a dissolution profile in the mouth, feel when applied in the mouth, and texture of the film, without deteriorating the film properties required as the oral film-form base and the oral film-form preparation, such as tensile strength and stiffness.

BRIEF DESCRIPTION OF DRAWINGS

FIG. 1 is a schematic view illustrating an embodiment of the oral film-form base of the present invention.

DESCRIPTION OF EMBODIMENTS

The present invention will be more specifically described by means of the following Examples which, however, are not intended to limit the scope of the present invention.

The foaming agents, auxiliary foaming agents, and particles of sugar alcohols were used in Examples and Comparative Examples after they were pulverized, and then subjected to screening with a sieve (32 μm or 90 μm), or made into fine particles using a jet mill (Spiral Jet Mill 50AS of Hosokawa Micron Corp.) or a spray dryer (Mini Spray Drier B-290 of BUCHI Labortechnik AG).

The particles were measured for the 50 vol % average particle size with a laser-scattering particle size distribution analyzer. The resulting value was used as the particle size index of the respective particles. Table 2 shows the 50 vol % average particle sizes of the foaming agents, the auxiliary foaming agents, and the particles of sugar alcohols used.

TABLE 2

| Foaming agent and auxiliary foaming agent | 50% Average particle size [um] |
|---|---|
| Sodium hydrogen carbonate fine particles | 6 |
| Sodium carbonate fine particles | 5 |
| Calcium carbonate fine particles | 3 |
| Potassium carbonate fine particles | 4 |
| Potassium hydrogen carbonate fine particles | 6 |
| Magnesium carbonate fine particles | 7 |
| Ammonium carbonate fine particles | 4 |
| Citric acid fine particles | 8 |
| DL-malic acid fine particles | 6 |
| Adipic acid fine particles | 9 |
| L-ascorbic acid fine particles | 7 |
| L-aspartic acid fine particles | 3 |
| L-glutamic acid fine particles | 5 |
| Glucono-delta-lactone fine particles | 2 |
| Glucuronic acid fine particles | 2 |
| Galacturonic acid fine particles | 5 |
| L-tartaric acid fine particles | 5 |
| Potassium L-bitartrate fine particles | 8 |
| Potassium L-bitartrate fine particles A | 2 |
| Potassium L-bitartrate fine particles B | 27 |
| Potassium L-bitartrate coarse particles | 91 |
| Calcium dihydrogen pyrophosphate fine particles | 5 |
| Succinic acid fine particles | 7 |
| Fumaric acid fine particles | 6 |
| Monosodium fumarate fine particles | 7 |
| Potassium aluminum sulfate fine particles | 8 |
| Sodium DL-malate fine particles | 5 |
| Potassium dihydrogen phosphate fine particles | 6 |
| Dipotassium hydrogen phosphate fine particles | 5 |
| Sodium dihydrogen phosphate fine particles | 7 |
| Disodium hydrogen phosphate fine particles | 7 |
| D-mannitol fine particles | 5 |

Example 1

To 240 parts by weight of ethanol were added 5 parts by weight of polyethylene glycol (PEG400), 10 parts by weight of sodium hydrogen carbonate fine particles with a previously controlled particle size (product of Wako Pure Chemical Industries Co., Ltd.), and 10 parts by weight of potassium L-bitartrate fine particles (product of Komatsuya Corporation), and dispersed well by ultrasonic agitation. Then, 75 parts by weight of HPC (product of Nippon Soda Co., Ltd., bland name: Nisso HPC SSL) having a molecular weight of about 30,000 and a hydroxypropoxy group-substitution degree of 53.4 to 77.5% was added, and stirred and dissolved with a rolling mixer to prepare a dispersion. After sufficient deaeration of the dispersion, it was spread onto a polyester release film and dried to prepare a film with a thickness of about 70 μm.

The resulting film was released from the polyester release film, and cut into a 4 $cm^2$ rectangle to obtain an oral film-form base of Example 1.

Example 2

An oral film-form base of Example 2 was prepared in the same manner as in Example 1, except that PVP (product of Wako Pure Chemical Industries Co., Ltd., reagent name: polyvinyl pyrrolidone K90) having a molecular weight of 1,050,000 to 1,200,000 was used in place of the HPC to make the composition shown in Table 3.

Example 3

An oral film-form base of Example 3 was prepared in the same manner as in Example 1, except that acetone was used in place of the ethanol to make the composition shown in Table 3.

Comparative Example 1

To 320 parts by weight of ethanol was added 6 parts by weight of polyethylene glycol (PEG400), and stirred well. Then, 94 parts by weight of HPC (product of Nippon Soda Co., Ltd., bland name: Nisso HPC SSL) having a molecular weight of about 30,000 and a hydroxypropoxy group-substitution degree of 53.4 to 77.5% was added, and stirred and dissolved with a rolling mixer to prepare a dispersion. After sufficient deaeration of the dispersion, it was spread onto a polyester release film and dried to prepare a film with a thickness of about 70 μm. The resulting film was released from the polyester release film, and cut into a 4 $cm^2$ rectangle to obtain an oral film-form base of Comparative Example 1.

Comparative Example 2

To 260 parts by weight of purified water were added 5 parts by weight of polyethylene glycol (PEG400), 10 parts by weight of sodium hydrogen carbonate fine particles with a previously controlled particle size (product of Wako Pure Chemical Industries Co., Ltd.), and 10 parts by weight of potassium L-bitartrate fine particles (product of Komatsuya Corporation), and dispersed well by ultrasonic agitation to find that foaming occurred and all the components were dissolved. Then, 75 parts by weight of pullulan (product of Hayashibara Co., Ltd., bland name: Food Additive pullulan) having a weight average molecular weight of 200,000 was added, and stirred and dissolved with a rolling mixer to prepare a solution. After sufficient deaeration of the solution, it was spread onto a polyester release film and dried to prepare a film with a thickness of about 70 μm.

The resulting film was released from the polyester release film, and cut into a 4 cm² rectangle to obtain an oral film-form base of Comparative Example 2.

Comparative Example 3

An oral film-form base of Comparative Example 3 was prepared in the same manner as in Comparative Example 2, except that HPMC (product of Shin-Etsu Chemical Co., Ltd., bland name: TC-5E) having a molecular weight of 16,000, a methoxy group-substitution degree of 28.0 to 30.0%, and a hydroxypropoxy group-substitution degree of 7.0 to 12.0% was used in place of the pullulan to make the composition shown in Table 3.

TABLE 3

| Components | Example [parts by weight] | | | Comparative Example [parts by weight] | | |
|---|---|---|---|---|---|---|
| | 1 | 2 | 3 | 1 | 2 | 3 |
| HPC | 75 | — | 75 | 94 | — | — |
| PVP K-30 | — | 75 | — | — | — | — |
| Pullulan | — | — | — | — | 75 | — |
| HPMC | — | — | — | — | — | 75 |
| PEG400 | 5 | 5 | 5 | 6 | 5 | 5 |
| Sodium hydrogen carbonate fine particles | 10 | 10 | 10 | — | 10 | 10 |
| Potassium L-bitartrate fine particles | 10 | 10 | 10 | — | 10 | 10 |
| Purified water | — | — | — | — | 260 | 260 |
| Ethanol | 240 | 200 | — | 320 | — | — |
| Acetone | — | — | 220 | — | — | — |

Example 4

To 240 parts by weight of ethanol were added 5 parts by weight of polyethylene glycol (PEG400), 10 parts by weight of sodium carbonate fine particles with a previously controlled particle size (product of Wako Pure Chemical Industries Co., Ltd.), and 10 parts by weight of potassium L-bitartrate fine particles (product of Komatsuya Corporation), and dispersed well by ultrasonic agitation. Then, 75 parts by weight of HPC (product of Nippon Soda Co., Ltd., bland name: Nisso HPC SSL) having a molecular weight of about 30,000 and a hydroxypropoxy group-substitution degree of 53.4 to 77.5% were added, and stirred and dissolved with a rolling mixer to prepare a dispersion. After sufficient deaeration of the dispersion, it was spread onto a polyester release film and dried to prepare a film with a thickness of about 70 μm.

The resulting film was released from the polyester release film, and cut into a 4 cm² rectangle to obtain an oral film-form base of Example 4.

Examples 5 to 9

Oral film-form bases of Examples 5 to 9 were prepared in the same manner as in Example 4, except that calcium carbonate fine particles (product of Bihoku Funka Kogyo Co., Ltd.) were used in Example 5, potassium carbonate fine particles (product of Wako Pure Chemical Industries Co., Ltd.) were used in Example 6, potassium hydrogen carbonate fine particles (product of Wako Pure Chemical Industries Co., Ltd.) were used in Example 7, magnesium carbonate fine particles (product Wako Pure Chemical Industries Co., Ltd.) were used in Example 8, and ammonium carbonate fine particles (product of Wako Pure Chemical Industries Co., Ltd.) were used in Example 9, in place of the sodium carbonate particles to make the compositions shown in Table 4.

TABLE 4

| Components | Example [parts by weight] | | | | | |
|---|---|---|---|---|---|---|
| | 4 | 5 | 6 | 7 | 8 | 9 |
| HPC | 75 | 75 | 75 | 75 | 75 | 75 |
| PEG400 | 5 | 5 | 5 | 5 | 5 | 5 |
| Sodium carbonate fine particles | 10 | — | — | — | — | — |
| Calcium carbonate fine particles | — | 10 | — | — | — | — |
| Potassium carbonate fine particles | — | — | 10 | — | — | — |
| Potassium hydrogen carbonate fine particles | — | — | — | 10 | — | — |
| Magnesium carbonate fine particles | — | — | — | — | 10 | — |
| Ammonium carbonate fine particles | — | — | — | — | — | 10 |
| Potassium L-bitartrate fine particles | 10 | 10 | 10 | 10 | 10 | 10 |
| Ethanol | 240 | 240 | 240 | 240 | 240 | 240 |

Example 10

To 240 parts by weight of ethanol were added 5 parts by weight of polyethylene glycol (PEG400), 10 parts by weight of sodium hydrogen carbonate fine particles with a previously controlled particle size (product of Wako Pure Chemical Industries Co., Ltd.), and 10 parts by weight of L-ascorbic acid fine particles (product of Wako Pure Chemical Industries Co., Ltd.), and dispersed well by ultrasonic agitation. Then, 75 parts by weight of HPC (product of Nippon Soda Co., Ltd., bland name: Nisso HPC SSL) having a molecular weight of about 30,000 and a hydroxypropoxy group-substitution degree of 53.4 to 77.5% was added, and stirred and dissolved with a rolling mixer to prepare a dispersion. After sufficient deaeration of the dispersion, it was spread onto a polyester release film and dried to prepare a film with a thickness of about 70 μm.

The resulting film was released from the polyester release film, and cut into a 4 cm² rectangle to obtain an oral film-form base of Example 10.

Examples 11 to 23

Oral film-form bases of Examples 11 to 23 were prepared in the same manner as in Example 10, except that L-aspartic acid fine particles (product of Bihoku Funka Kogyo Co., Ltd.) were used in Example 11, L-glutamic acid fine particles (product of Ajinomoto Healthy Supply, Inc.) were used in Example 12, galacturonic acid fine particles (product of Wako Pure Chemical Industries Co., Ltd.) were used in Example 13, glucuronic acid fine particles (product of Alfer Aesar) were used in Example 14, glucono-δ-lactone fine particles (product of Wako Pure Chemical Industries Co., Ltd.) were used in Example 15, calcium dihydrogen pyrophosphate fine particles (product of Kirin Kyowa Foods Company Limited) were used in Example 16, monosodium fumarate fine particles (product of Nippon Shokubai Co., Ltd) were used in Example 17, potassium aluminum sulfate fine particles (product of Wako Pure Chemical Industries Co., Ltd.) were used in Example 18, sodium DL-malate fine particles (product of Wako Pure Chemical Industries Co., Ltd.) were used in Example 19, potassium dihydrogen phosphate fine particles (product of Wako Pure Chemical Industries Co., Ltd.) were used in Example 20, dipotassium hydrogen phosphate fine particles (product of Wako Pure Chemical Industries Co., Ltd.) were used in Example 21, sodium dihydrogen phosphate fine particles (product of Wako Pure Chemical Industries Co., Ltd.) were used in Example 22, and disodium hydrogen phosphate fine particles (product of Wako Pure Chemical Industries Co., Ltd.) were used in Example 23, in place of the L-ascorbic acid fine particles to make the compositions shown in Table 5.

Example 4, except that DL-malic acid fine particles (product of Wako Pure Chemical Industries Co., Ltd.) were used in Comparative Examples, adipic acid fine particles (product of Wako Pure Chemical Industries Co., Ltd.) were used in Comparative Example 6, succinic acid fine particles (product of Fuso Chemical Co., Ltd.) were used in Comparative Example 7, fumaric acid fine particles (product of Wako Pure Chemical Industries Co., Ltd.) were used in Comparative Example 8, and L-tartaric acid fine particles (product of Wako Pure Chemical Industries Co., Ltd.) were used in Comparative Example 9, in place of the citric acid fine particles to make the compositions shown in Table 6.

TABLE 5

| Components | Example [parts by weight] | | | | | | | | | | | | | |
|---|---|---|---|---|---|---|---|---|---|---|---|---|---|---|
| | 10 | 11 | 12 | 13 | 14 | 15 | 16 | 17 | 18 | 19 | 20 | 21 | 22 | 23 |
| HPC | 75 | 75 | 75 | 75 | 75 | 75 | 75 | 75 | 75 | 75 | 75 | 75 | 75 | 75 |
| PEG400 | 5 | 5 | 5 | 5 | 5 | 5 | 5 | 5 | 5 | 5 | 5 | 5 | 5 | 5 |
| Sodium hydrogen carbonate fine particles | 10 | 10 | 10 | 10 | 10 | 10 | 10 | 10 | 10 | 10 | 10 | 10 | 10 | 10 |
| L-ascorbic acid fine particles | 10 | — | — | — | — | — | — | — | — | — | — | — | — | — |
| L-aspartic acid fine particles | — | 10 | — | — | — | — | — | — | — | — | — | — | — | — |
| L-glutamic acid fine particles | — | — | 10 | — | — | — | — | — | — | — | — | — | — | — |
| Galacturonic acid fine particles | — | — | — | 10 | — | — | — | — | — | — | — | — | — | — |
| Glucuronic acid fine particles | — | — | — | — | 10 | — | — | — | — | — | — | — | — | — |
| Glucono-delta-lactone fine particles | — | — | — | — | — | 10 | — | — | — | — | — | — | — | — |
| Calcium dihydrogen pyrophosphate fine particles | — | — | — | — | — | — | 10 | — | — | — | — | — | — | — |
| Monosodium fumarate fine particles | — | — | — | — | — | — | — | 10 | — | — | — | — | — | — |
| Potassium aluminum sulfate fine particles | — | — | — | — | — | — | — | — | 10 | — | — | — | — | — |
| Sodium DL-malate fine particles | — | — | — | — | — | — | — | — | — | 10 | — | — | — | — |
| Potassium dihydrogen phosphate fine particles | — | — | — | — | — | — | — | — | — | — | 10 | — | — | — |
| Dipotassium hydrogen phosphate fine particles | — | — | — | — | — | — | — | — | — | — | — | 10 | — | — |
| Sodium dihydrogen phosphate fine particles | — | — | — | — | — | — | — | — | — | — | — | — | 10 | — |
| Disodium hydrogen phosphate fine particles | — | — | — | — | — | — | — | — | — | — | — | — | — | 10 |
| Ethanol | 240 | 240 | 240 | 240 | 240 | 240 | 240 | 240 | 240 | 240 | 240 | 240 | 240 | 240 |

Comparative Example 4

To 240 parts by weight of ethanol were added 5 parts by weight of polyethylene glycol (PEG400), 10 parts by weight of sodium hydrogen carbonate fine particles with a previously controlled particle size (product of Wako Pure Chemical Industries Co., Ltd.), and 10 parts by weight of citric acid fine particles (product of Wako Pure Chemical Industries Co., Ltd.), and dispersed well by ultrasonic agitation. Then, 75 parts by weight of HPC (product of Nippon Soda Co., Ltd., bland name: Nisso HPC SSL) having a molecular weight of about 30,000 and a hydroxypropoxy group-substitution degree of 53.4 to 77.5% was added, and stirred and dissolved with a rolling mixer to prepare a dispersion. After sufficient deaeration of the dispersion, it was spread onto a polyester release film and dried to prepare a film with a thickness of about 70 μm.

The resulting film was released from the polyester release film, and cut into a 4 cm² rectangle to obtain an oral film-form base of Comparative Example 4.

Comparative Examples 5 to 9

Oral film-form bases of Comparative Examples 5 to 9 were prepared in the same manner as in Comparative

TABLE 6

| Components | Comparative Example [parts by weight] | | | | | |
|---|---|---|---|---|---|---|
| | 4 | 5 | 6 | 7 | 8 | 9 |
| HPC | 75 | 75 | 75 | 75 | 75 | 75 |
| PEG400 | 5 | 5 | 5 | 5 | 5 | 5 |
| Sodium hydrogen carbonate fine particles | 10 | 10 | 10 | 10 | 10 | 10 |
| Citric acid fine particles | 10 | — | — | — | — | — |
| DL-malic acid fine particles | — | 10 | — | — | — | — |
| Adipic acid fine particles | — | — | 10 | — | — | — |
| Succinic acid fine particles | — | — | — | 10 | — | — |
| Fumaric acid fine particles | — | — | — | — | 10 | — |
| L-tartaric acid fine particles | — | — | — | — | — | 10 |
| Ethanol | 240 | 240 | 240 | 240 | 240 | 240 |

Example 24

To 240 parts by weight of ethanol were added 5 parts by weight of polyethylene glycol (PEG400), 10 parts by weight of sodium hydrogen carbonate fine particles with a previously controlled particle size (product of Wako Pure Chemical Industries Co., Ltd.), and 10 parts by weight of potassium L-bitartrate fine particles A (product of Komatsuya Corporation), and dispersed well by ultrasonic agitation. Then, 75 parts by weight of HPC (product of Nippon Soda Co., Ltd., bland name: Nisso HPC SSL) having a molecular weight of about 30,000 and a hydroxypropoxy group-substitution degree of 53.4 to 77.5% was added, and stirred and dissolved with a rolling mixer to prepare a dispersion. After sufficient deaeration of the dispersion, it was spread onto a polyester release film and dried to prepare a film with a thickness of about 70 μm.

The resulting film was released from the polyester release film, and cut into a 4 cm² rectangle to obtain an oral film-form base of Example 24.

Example 25, Comparative Example 10

Oral film-form bases of Example 25 and Comparative Example 10 were prepared in the same manner as in Example 24, except that potassium L-bitartrate fine particles B (product of Komatsuya Corporation) were used in Example 25, and potassium L-bitartrate coarse particles (product of Komatsuya Corporation) were used in Comparative Example 10, in place of the sodium carbonate particles to make the compositions shown in Table 7.

Example 26

To 270 parts by weight of ethanol were added 6 parts by weight of polyethylene glycol (PEG400), 5 parts by weight of sodium hydrogen carbonate fine particles with a previously controlled particle size (product of Wako Pure Chemical Industries Co., Ltd.), and 5 parts by weight of potassium L-bitartrate fine particles A (product of Komatsuya Corporation), and dispersed well by ultrasonic agitation. Then, 84 parts by weight of HPC (product of Nippon Soda Co., Ltd., bland name: Nisso HPC SSL) having a molecular weight of about 30,000 and a hydroxypropoxy group-substitution degree of 53.4 to 77.5% was added, and stirred and dissolved with a rolling mixer to prepare a dispersion. After sufficient deaeration of the dispersion, it was spread onto a polyester release film and dried to prepare a film with a thickness of about 70 μm.

The resulting film was released from the polyester release film, and cut into a 4 cm² rectangle to obtain an oral film-form base of Example 26.

Example 27

To 220 parts by weight of ethanol were added 4 parts by weight of polyethylene glycol (PEG400), 15 parts by weight of sodium hydrogen carbonate fine particles with a previously controlled particle size (product of Wako Pure Chemical Industries Co., Ltd.), and 15 parts by weight of potassium L-bitartrate fine particles A (product of Komatsuya Corporation), and dispersed well by ultrasonic agitation. Then, 66 parts by weight of HPC (product of Nippon Soda Co., Ltd., bland name: Nisso HPC SSL) having a molecular weight of about 30,000 and a hydroxypropoxy group-substitution degree of 53.4 to 77.5% was added, and stirred and dissolved with a rolling mixer to prepare a dispersion. After sufficient deaeration of the dispersion, it was spread onto a polyester release film and dried to prepare a film with a thickness of about 70 μm.

The resulting film was released from the polyester release film, and cut into a 4 cm² rectangle to obtain an oral film-form base of Example 27.

Example 28

To 160 parts by weight of ethanol were added 3 parts by weight of polyethylene glycol (PEG400), 25 parts by weight of sodium hydrogen carbonate fine particles with a previously controlled particle size (product of Wako Pure Chemical Industries Co., Ltd.), and 25 parts by weight of potassium L-bitartrate fine particles A (product of Komatsuya Corporation), and dispersed well by ultrasonic agitation. Then, 47 parts by weight of HPC (product of Nippon Soda Co., Ltd., bland name: Nisso HPC SSL) having a molecular weight of about 30,000 and a hydroxypropoxy group-substitution degree of 53.4 to 77.5% was added, and stirred and dissolved with a rolling mixer to prepare a dispersion. After sufficient deaeration of the dispersion, it was spread onto a polyester release film and dried to prepare a film with a thickness of about 70 μm.

The resulting film was released from the polyester release film, and cut into a 4 cm² rectangle to obtain an oral film-form base of Example 28.

Example 29

To 160 parts by weight of ethanol were added 3 parts by weight of polyethylene glycol (PEG400), 10 parts by weight of sodium hydrogen carbonate fine particles with a previously controlled particle size (product of Wako Pure Chemical Industries Co., Ltd.), 10 parts by weight of potassium L-bitartrate fine particles A (product of Komatsuya Corporation), and 30 parts by weight of D-mannitol fine particles (product of ROQUETTE), and dispersed well by ultrasonic agitation. Then, 47 parts by weight of HPC (product of Nippon Soda Co., Ltd., bland name: Nisso HPC SSL) having a molecular weight of about 30,000 and a hydroxypropoxy group-substitution degree of 53.4 to 77.5% was added, and stirred and dissolved with a rolling mixer to prepare a dispersion. After sufficient deaeration of the dispersion, it was spread onto a polyester release film and dried to prepare a film with a thickness of about 70 μm.

The resulting film was released from the polyester release film, and cut into a 4 cm² rectangle to obtain an oral film-form base of Example 29.

TABLE 7

| Components | Example [parts by weight] 24 | Example [parts by weight] 25 | Comparative Example [parts by weight] 10 | Example [parts by weight] 26 | Example [parts by weight] 27 | Example [parts by weight] 28 | Example [parts by weight] 29 |
|---|---|---|---|---|---|---|---|
| HPC | 75 | 75 | 75 | 84 | 66 | 47 | 47 |
| PEG400 | 5 | 5 | 5 | 6 | 4 | 3 | 3 |
| Sodium hydrogen carbonate fine particles | 10 | 10 | 10 | 5 | 15 | 25 | 10 |
| Potassium L-bitartrate fine particles A | 10 | — | — | 5 | 15 | 25 | 10 |
| Potassium L-bitartrate fine particles B | — | 10 | — | — | — | — | — |

TABLE 7-continued

|  | Example [parts by weight] | | Comparative Example [parts by weight] | Example [parts by weight] | | | |
|---|---|---|---|---|---|---|---|
| Components | 24 | 25 | 10 | 26 | 27 | 28 | 29 |
| Potassium L-bitartrate coarse particles | — | — | 10 | — | — | — | — |
| D-mannitol fine particles | — | — | — | — | — | — | 30 |
| Ethanol | 240 | 240 | 240 | 270 | 220 | 160 | 160 |

Example 30

To 140 parts by weight of ethanol were added 4 parts by weight of polyethylene glycol (PEG400), 50 parts by weight of diphenhydramine hydrochloride (product of Wako Pure Chemical Industries Co., Ltd.), 0.3 parts by weight of sucralose (product of San-Ei Gen F.F.I., Inc), 2 parts by weight of sodium hydrogen carbonate fine particles with a previously controlled particle size (product of Wako Pure Chemical Industries Co., Ltd.), 2 parts by weight of potassium L-bitartrate fine particles (product of Komatsuya Corporation), and 5.0 parts by weight of D-mannitol fine particles (product of ROQUETTE), and dispersed well by ultrasonic agitation. Then, 36.7 parts by weight of HPC (product of Nippon Soda Co., Ltd., bland name: Nisso HPC SSL) having a molecular weight of about 30,000 and a hydroxypropoxy group-substitution degree of 53.4 to 77.5% was added, and stirred and dissolved with a rolling mixer to prepare a dispersion. After sufficient deaeration of the dispersion, it was spread onto a polyester release film and dried to prepare a film with a thickness of about 70 μm.

The resulting film was released from the polyester release film, and cut into a 4 cm² rectangle to obtain an oral film-form preparation of Example 30.

Examples 31 to 37

Oral film-form preparations of Examples 31 to 37 were prepared in the same manner as in Example 30, except that granisetron hydrochloride (product of Cipla Ltd.) was used in Example 31, tolterodine tartrate (product of Ferrer) was used in Example 32, scopolamine hydrobromide (product of Wako Pure Chemical Industries Co., Ltd.) was used in Example 33, famotidine (product of Wako Pure Chemical Industries Co., Ltd.) was used in Example 34, zolmitriptan (product of Cipla Ltd.) was used in Example 35, sodium montelukast (product of LG Life Sciences) was used in Example 36, and epinephrine (product of LKT Laboratories) was used in Example 37, in place of the diphenhydramine hydrochloride to make the compositions shown in Table 8.

TABLE 8

| Components | Example [parts by weight] | | | | | | | |
|---|---|---|---|---|---|---|---|---|
|  | 30 | 31 | 32 | 33 | 34 | 35 | 36 | 37 |
| Diphenhydramine hydrochloride | 50.0 | — | — | — | — | — | — | — |
| Granisetron hydrochloride | — | 10.0 | — | — | — | — | — | — |
| Tolterodine tartrate | — | — | 13.3 | — | — | — | — | — |
| Scopolamine hydrobromide | — | — | — | 0.8 | — | — | — | — |
| Famotidine | — | — | — | — | 25.0 | — | — | — |
| Zolmitriptan | — | — | — | — | — | 10.0 | — | — |
| Sodium montelukast | — | — | — | — | — | — | 13.0 | — |
| Epinephrine | — | — | — | — | — | — | — | 1.3 |
| HPC | 36.7 | 40.7 | 37.4 | 39.9 | 40.7 | 40.7 | 37.7 | 39.4 |
| PEG400 | 4.0 | 4.0 | 4.0 | 4.0 | 4.0 | 4.0 | 4.0 | 4.0 |
| Sodium hydrogen carbonate fine particles | 2.0 | 5.0 | 5.0 | 10.0 | 5.0 | 5.0 | 5.0 | 10.0 |
| Potassium L-bitartrate fine particles | 2.0 | 5.0 | 5.0 | 10.0 | 5.0 | 5.0 | 5.0 | 10.0 |
| Sucralose | 0.3 | 0.3 | 0.3 | 0.3 | 0.3 | 0.3 | 0.3 | 0.3 |
| D-mannitol fine particles | 5.0 | 35.0 | 35.0 | 35.0 | 20.0 | 35.0 | 35.0 | 35.0 |
| Ethanol | 140.0 | 160.0 | 155.0 | 160.0 | 160.0 | 160.0 | 155.0 | 160.0 |

The oral film-form bases and the oral film-form preparations prepared in examples and comparative examples were measured and evaluated for releasability from polyester release films, film flexibility, film strength, dissolution profile in the mouth, appearance, foaming property in the mouth, and taking property, through measurements by peeling property test, stiffness test, tensile strength test, oral dissolution test, sensory evaluation (appearance), sensory evaluation (foaming property), and sensory evaluation (taste), respectively.

(1) Peeling Property Evaluation

Each sample of the oral film-form bases and the oral film-form preparations was released from the polyethylene terephthalate release film during production thereof so that the peeling property was evaluated and given a score using the following criteria. The peeling property herein indicates whether or not oral film-form bases and oral film-form preparations can be produced. Therefore, if the added foaming agent, auxiliary foaming agent, or sugar alcohol particles was/were dissolved and recrystallized after drying during the production, or if the dissolved materials plasticized the film, the peeling property would be deteriorated.

[Evaluation Criteria]
4: Can be released off easily
3: Can be released off
2: Can be released off with some effort
1: Can be released off with effort, but film tears
0: Cannot be released off at all (2) Stiffness Test This test was performed following the test method of "JIS L1096 Testing Methods for Woven Fabrics, 8.19 Stiffness, 8.19.1 Method A (45° cantilever method)."

In this test, five sheets of 20 mm×150 mm test pieces were collected from the sample of each of the Examples and Comparative Examples. The short dimension of each test piece was aligned with the baseline of the scale on a smooth-surfaced, flat platform with one end having a 45° downward slope.

Next, the test piece was gently slid in the direction of the slope by a suitable method, and when the center point of an edge of the test piece came into contact with the slope A, the position of the trailing edge was read on the scale. Stiffness is expressed as the length (mm) that the test piece was moved. Stiffness was determined by measuring the moved distances of the five test pieces both face up and face down both forward and backward, and then calculating the mean value. The evaluation criteria were based on the stiffness (about 60 mm), and are listed below.

[Evaluation Criteria]
4: 60±10 mm or more, less than 60±20 mm
3: 60±20 mm or more, less than 60±30 mm
2: 60±30 mm or more, less than 60±40 mm
1: 60±40 mm or more (3) Tensile Strength Test This test was carried out following "JIS K7127 Testing Method for Tensile Properties of Plastic Films and Sheets." Each of the film-form bases and preparations was cut into a 12 mm×50 mm test sample, and the test was performed thereon after thorough drying in a desiccator.

A small, tabletop vertical tensile test apparatus (produced by Shimadzu Corporation, EZ TEST-100M) was used to perform the test at a draw rate of 60 mm/min. Because almost no stretching was seen in the test samples, the tensile strength at the measured yield point was used as the tensile strength value. The test was repeated three times for each sample, and the mean value was determined as the tensile strength. The tensile strength was then converted into a score using the following criteria.

[Evaluation Criteria]
4: Tensile strength=10 N or more, less than 20 N
3: Tensile strength=5 N or more, less than 10 N
2: Tensile strength=2 N or more, less than 5 N
1: Tensile strength=less than 2 N (4) Oral Dissolution Test First, 900 mL of a pH 6.8 phosphate buffer was placed in a 1000-mL glass petri dish, a stainless steel mesh basket (Φ4 mm) was inverted and submerged therein, and agitation was provided by a stirrer (300 rpm). The temperature of the liquid was maintained at 37±2° C. using a constant temperature water circulator. A test piece (3 cm$^2$) was submerged in the liquid, and concurrently a 3 cm×3 cm stainless steel screen (5 mm mesh) was placed on top as a sinker.

The disintegration of the test piece was checked visually, and the duration from the time the test piece was submerged until the test piece had finished disintegrating was measured with a stopwatch. The measurement of each sample was repeated three times, and the mean value thereof was used as the oral dissolution time. The oral dissolution time was converted into a score using the following criteria.

[Evaluation Criteria]
4: Oral dissolution time=shorter than 10 sec.
3: Oral dissolution time=10 sec. or longer, shorter than 15 sec.
2: Oral dissolution time=15 sec. or longer, shorter than 20 sec.
1: Oral dissolution time=20 sec. or longer (5) Sensory Evaluation (Appearance)

The oral film-form bases and the oral film-form preparations were visually observed and evaluated on whether or not the added foaming agent, auxiliary foaming agent, or sugar alcohol particles was/were dissolved and recrystallized after drying during the production based on the criteria below. The particle size of crystals was obtained by measuring the longest diameter of the crystal using a microscope (product of Keyence Corp., model VHX-600).

[Evaluation Criteria]
4: No crystal is found.
3: Slight recrystallization is found but the crystal has a size of 1 mm or smaller.
2: Recrystallization is clearly found but the crystal has a size of 1 mm or smaller.
1: A large number of crystals having a size of more than 1 mm are found.

(6) Sensory Evaluation (Foaming Property)

The oral film-form bases and the oral film-form preparations each were placed in a beaker containing 10 mL of distilled water to evaluate the foaming property based on the following criteria.

[Evaluation Criteria]
4: Sufficient foaming occurs upon starting of the test.
3: The amount of foaming is slightly small but acceptable.
2: Foaming is barely recognizable by close watching.
1: No foaming occurs.

(7) Sensory Evaluation (Taste)

Study participants took each of the oral film-form bases or the oral film-form preparations to evaluate the taste based on the criteria below. After recognizing the taste, the study participants spilled out the base or preparation, and washed the mouth with purified water.

[Evaluation Criteria]
4: Tastes good or nothing
3: Tastes slightly peculiar but is acceptable
2: Tastes peculiar and slightly distasteful
1: Tastes distasteful Table 9 shows the evaluation results of the tests (1) to (7) performed on the oral film-form bases in Examples 1 to 9 and Comparative Examples 1 to 3.

TABLE 9

| Sample | Peeling property | Stiffness | Tensile strength | Oral dissolution | Appearance | Taking property (Foaming property) | Taking property (Taste) | Total |
| --- | --- | --- | --- | --- | --- | --- | --- | --- |
| Example 1 | 4 | 4 | 4 | 4 | 4 | 4 | 4 | 28 |
| Example 2 | 3 | 4 | 3 | 4 | 4 | 3 | 4 | 25 |
| Example 3 | 4 | 4 | 4 | 4 | 4 | 4 | 4 | 28 |
| Example 4 | 4 | 4 | 4 | 4 | 4 | 3 | 4 | 27 |
| Example 5 | 4 | 4 | 4 | 3 | 4 | 2 | 4 | 25 |
| Example 6 | 4 | 4 | 4 | 4 | 4 | 3 | 4 | 27 |
| Example 7 | 4 | 4 | 4 | 4 | 4 | 4 | 4 | 28 |
| Example 8 | 4 | 4 | 4 | 3 | 4 | 3 | 4 | 26 |
| Example 9 | 4 | 4 | 4 | 4 | 4 | 2 | 2 | 24 |

TABLE 9-continued

| Sample | Peeling property | Stiffness | Tensile strength | Oral dissolution | Appearance | Taking property (Foaming property) | Taking property (Taste) | Total |
|---|---|---|---|---|---|---|---|---|
| Comparative Example 1 | 4 | 4 | 4 | 1 | 4 | 1 | 3 | 21 |
| Comparative Example 2 | 3 | 2 | 2 | 1 | 1 | 1 | 4 | 14 |
| Comparative Example 3 | 2 | 2 | 2 | 1 | 1 | 1 | 4 | 13 |

All the oral film-form bases listed in Table 9 received good evaluation scores in the respective tests, except that the oral film-form base in Example 9 received a slightly bad evaluation score in the sensory tests. In contrast, the prepared film-form bases of Comparative Examples 1 to 3 did not foam at all because they had foamed when the foaming agent reacted with the auxiliary foaming agent during the production. That is, the oral film-form bases in Examples 1 to 9 are proved to have good peeling property, sufficient strength, good oral dissolution, and taking easiness.

Table 10 shows the evaluation results of the tests (1) to (7) performed on the oral film-form bases in Examples 10 to 23.

TABLE 10

| Sample | Peeling property | Stiffness | Tensile strength | Oral dissolution | Appearance | Taking property (Foaming property) | Taking property (Taste) | Total |
|---|---|---|---|---|---|---|---|---|
| Example 10 | 4 | 3 | 3 | 4 | 4 | 2 | 4 | 24 |
| Example 11 | 4 | 4 | 4 | 4 | 4 | 4 | 4 | 28 |
| Example 12 | 4 | 4 | 4 | 4 | 4 | 4 | 3 | 27 |
| Example 13 | 4 | 4 | 4 | 4 | 4 | 4 | 4 | 28 |
| Example 14 | 4 | 4 | 4 | 4 | 4 | 4 | 4 | 28 |
| Example 15 | 4 | 3 | 3 | 4 | 4 | 3 | 4 | 25 |
| Example 16 | 4 | 4 | 4 | 3 | 4 | 3 | 4 | 26 |
| Example 17 | 4 | 4 | 4 | 4 | 4 | 3 | 4 | 27 |
| Example 18 | 4 | 4 | 4 | 4 | 4 | 3 | 3 | 26 |
| Example 19 | 4 | 4 | 4 | 4 | 4 | 3 | 2 | 25 |
| Example 20 | 4 | 4 | 4 | 4 | 4 | 4 | 2 | 26 |
| Example 21 | 4 | 4 | 4 | 4 | 4 | 4 | 2 | 26 |
| Example 22 | 4 | 4 | 4 | 4 | 4 | 4 | 4 | 28 |
| Example 23 | 4 | 4 | 4 | 4 | 4 | 4 | 4 | 28 |

All the oral film-form bases listed in Table 10 received good evaluation scores in the respective tests, except that the oral film-form base in Example 10 received a slightly bad evaluation score in the taking property (foaming property), and the oral film-form bases in Example 19 to 21 received slightly bad evaluation scores in the taking property (taste).

Table 11 shows the evaluation results of the tests (1) to (7) performed on the oral film-form bases in Comparative Examples 4 to 9.

TABLE 11

| Sample | Peeling property | Stiffness | Tensile strength | Oral dissolution | Appearance | Taking property (Foaming property) | Taking property (Taste) | Total |
|---|---|---|---|---|---|---|---|---|
| Comparative Example 4 | 3 | 3 | 2 | 3 | 2 | 2 | 4 | 19 |
| Comparative Example 5 | 3 | 2 | 2 | 3 | 2 | 2 | 4 | 18 |
| Comparative Example 6 | 2 | 3 | 3 | 3 | 2 | 2 | 3 | 18 |
| Comparative Example 7 | 2 | 2 | 3 | 3 | 3 | 2 | 4 | 19 |
| Comparative Example 8 | 2 | 2 | 3 | 3 | 3 | 2 | 3 | 18 |
| Comparative Example 9 | 3 | 3 | 2 | 3 | 2 | 2 | 4 | 19 |

The oral film-form preparations in Comparative Examples 4 to 9 listed in Table 11 received unfavorable evaluation scores in the respective tests. The disintegration aid used herein is soluble in ethanol used during the production, and thus probably it reacted with a disintegrator to foam during the production, or it was recrystallized after drying, thereby affecting the evaluations.

Table 12 shows the evaluation results of the tests (1) to (7) performed on the oral film-form bases in Examples 24 to 29 and Comparative Example 10.

TABLE 12

| Sample | Peeling property | Stiffness | Tensile strength | Oral dissolution | Appearance | Taking property (Foaming property) | Taking property (Taste) | Total |
| --- | --- | --- | --- | --- | --- | --- | --- | --- |
| Example 24 | 4 | 4 | 4 | 4 | 4 | 4 | 4 | 28 |
| Example 25 | 4 | 4 | 3 | 4 | 4 | 4 | 4 | 27 |
| Comparative Example 10 | 4 | 2 | 1 | 4 | 2 | 3 | 4 | 20 |
| Example 26 | 4 | 4 | 4 | 4 | 4 | 4 | 4 | 28 |
| Example 27 | 4 | 4 | 4 | 4 | 4 | 4 | 4 | 28 |
| Example 28 | 4 | 4 | 3 | 4 | 4 | 4 | 4 | 27 |
| Example 29 | 4 | 4 | 4 | 4 | 4 | 4 | 4 | 28 |

All the oral film-form bases in Examples 24 to 29 listed in Table 12 received good evaluation scores in the respective tests. The oral film-form bases in Comparative Example 10 received low evaluation scores in the evaluations of stiffness, tensile strength, and appearance. This was considered because the disintegration aid had a large particle diameter, and this affected the physical properties of the film.

Table 13 shows the evaluation results of the tests (1) to (7) performed on the oral film-form preparations in Examples 30 to 37.

TABLE 13

| Sample | Peeling property | Stiffness | Tensile strength | Oral dissolution | Appearance | Taking property (Foaming property) | Taking property (Taste) | Total |
| --- | --- | --- | --- | --- | --- | --- | --- | --- |
| Example 30 | 4 | 3 | 3 | 4 | 3 | 3 | 3 | 23 |
| Example 31 | 4 | 4 | 4 | 3 | 4 | 4 | 4 | 27 |
| Example 32 | 4 | 4 | 3 | 4 | 4 | 4 | 4 | 27 |
| Example 33 | 4 | 4 | 4 | 4 | 4 | 4 | 4 | 28 |
| Example 34 | 4 | 3 | 3 | 3 | 4 | 4 | 4 | 25 |
| Example 35 | 4 | 4 | 4 | 4 | 4 | 4 | 4 | 28 |
| Example 36 | 4 | 4 | 4 | 4 | 4 | 4 | 4 | 28 |
| Example 37 | 4 | 4 | 4 | 4 | 4 | 4 | 4 | 28 |

All the oral film-form preparations of Examples 30 to 37 listed in Table 13 received good evaluation scores in the respective tests. Accordingly, it was proved that the present invention enables production of oral film-form preparations which have good peeling property, sufficient strength, good oral dissolution, and taking easiness, even in the case of using various agents.

INDUSTRIAL APPLICABILITY

The present invention can provide oral film-form bases and oral film-form preparations each of which has a sufficient film strength, shows rapid dissolving profile in the mouth, and provides improved taking easiness due to its foaming in the mouth.

REFERENCE SIGNS LIST

1a Particles of a foaming agent
1b Particles of an auxiliary foaming agent
1c Film

The invention claimed is:

1. An oral film-form preparation comprising an oral film-form base and a drug in the oral film-form base, wherein the oral film-form base comprises an edible polymer soluble both in water and in an organic solvent having a solubility parameter of 9.7 or higher, wherein the edible polymer is at least one of polyvinylpyrrolidone or hydroxypropyl cellulose, a foaming agent particle, and an auxiliary foaming agent particle, wherein the foaming agent particle is foamable in the presence of water, the foaming agent particle and the auxiliary foaming agent particle each are insoluble in the organic solvent, have an average particle size of 0.1 to 60 μm, and are included in particle states, the foaming agent particle and the auxiliary foaming agent particle are dispersed uniformly in a film containing the edible polymer and the drug, the foaming agent particle is at least one selected from the group consisting of sodium hydrogen carbonate, sodium carbonate, magnesium carbonate, ammonium hydrogen carbonate, ammonium carbonate, potassium carbonate, and calcium carbonate, and the auxiliary foaming agent particle is at least one selected from the group consisting of L-ascorbic acid, potassium L-bitartrate, calcium dihydrogen pyrophosphate, disodium dihydrogen pyrophosphate, galacturonic acid, glucuronic acid, monosodium fumarate, potassium aluminum sulfate, sodium DL-malate, potassium dihydrogen phosphate, and dipotassium hydrogen phosphate.

2. The oral film-form preparation according to claim 1, wherein the foaming agent particle and the auxiliary foaming agent particle each have an average particle size of 0.1 μm to 30 μm.

3. The oral film-form preparation according to claim 1, wherein the polyvinylpyrrolidone has a weight-average molecular weight of 2,500 to 3,000,000.

4. The oral film-form preparation according to claim 1, wherein the hydroxypropyl cellulose has a weight-average molecular weight of 10,000 to 1,200,000.

5. The oral film-form preparation according to claim 1, wherein the hydroxypropyl cellulose has a hydroxypropoxy substitution degree of 50 to 100%.

6. The oral film-form preparation according to claim 1, further comprising particles of at least one selected from the group consisting of mono- to hexasaccharide sugars and sugar alcohols thereof each having an average particle size of 0.1 to 60 μm.

7. An oral film-form preparation comprising an oral film-form base and a drug in the oral film-form base, wherein the oral film-form base comprises
an edible polymer soluble both in water and in an organic solvent having a solubility parameter of 9.7 or higher,
a foaming agent particle, and
an auxiliary foaming agent particle,
wherein the foaming agent particle is foamable in the presence of water,
the foaming agent particle and the auxiliary foaming agent particle each are insoluble in the organic solvent, have an average particle size of 0.1 to 60 μm, and are included in particle states,
the foaming agent particle and the auxiliary foaming agent particle are uniformly dispersed in a film containing the edible polymer and the drug, wherein the film is a dried film,
the foaming agent particle is at least one selected from the group consisting of sodium hydrogen carbonate, sodium carbonate, magnesium carbonate, ammonium hydrogen carbonate, ammonium carbonate, potassium carbonate, and calcium carbonate, and
the auxiliary foaming agent particle is at least one selected from the group consisting of L-ascorbic acid, potassium L-bitartrate, calcium dihydrogen pyrophosphate, disodium dihydrogen pyrophosphate, galacturonic acid, glucuronic acid, monosodium fumarate, potassium aluminum sulfate, sodium DL-malate, potassium dihydrogen phosphate, and dipotassium hydrogen phosphate.

* * * * *